United States Patent [19]

Curtis et al.

[11] 4,213,961
[45] Jul. 22, 1980

[54] ORAL COMPOSITIONS

[75] Inventors: Stephen N. Curtis, Edison; Hridaya N. Bhargava, East Brunswick, both of N.J.

[73] Assignee: Beecham, Inc., Clifton, N.J.

[21] Appl. No.: 889,205

[22] Filed: Mar. 23, 1978

[51] Int. Cl.$^2$ .......................... A61K 7/22; A61K 7/24
[52] U.S. Cl. ......................................... 424/54; 424/55
[58] Field of Search ...................................... 424/49–58

[56] References Cited

U.S. PATENT DOCUMENTS

| 1,528,422 | 3/1925 | Helsley | 424/55 |
| 2,470,906 | 5/1949 | Taylor | 424/55 |
| 3,886,265 | 5/1975 | Evers et al. | 424/49 |
| 3,887,701 | 6/1975 | Nachtigal | 424/54 |
| 3,925,543 | 12/1975 | Donohue | 424/52 |
| 3,934,002 | 1/1976 | Haefele | 424/54 |
| 3,937,807 | 2/1976 | Haefele | 424/52 |
| 3,957,967 | 5/1976 | L'Orange | 424/49 X |
| 4,025,616 | 5/1977 | Haefele | 424/52 |
| 4,051,234 | 9/1977 | Gieske et al. | 424/52 |
| 4,067,962 | 1/1978 | Juneja | 424/52 |

*Primary Examiner*—Shep K. Rose
*Attorney, Agent, or Firm*—Jacobs & Jacobs

[57] ABSTRACT

Oral compositions useful for controlling dental plaque and gingivitis and for preventing caries are produced comprising a cationic antimicrobial agent and a combination of anti-stain agents which reduce the staining effect of the cationic antimicrobial.

17 Claims, No Drawings

ORAL COMPOSITIONS

The present invention is concerned with oral compositions useful for controlling dental plaque and gingivitis and for preventing caries. The active agent is a cationic antimicrobial agent, such as bisbiguanides or quaternary ammonium compounds, which agents are known in the art to be useful for such purposes. It is also known in the art that cationic antimicrobial agents such as bisbiguanides and quaternary ammonium compounds have the disadvantage of staining teeth. The present invention provides an oral composition utilizing bisbiguanides or quaternary ammonium compounds together with a combination of anti-stain agents which exert an additive effect on stain reduction thus providing greater stain reduction than is provided by the individual anti-stain agents alone.

It is known in the art that bisbiguanides inhibit the formation of plaque and caries and that anti-calculus agents may be combined therewith to inhibit the tendency of the bisbiguanides to stain the oral surfaces. (See U.S. Pat. No. 3,934,002.) Among the anti-calculus agents disclosed in said patent are quaternary ammonium compounds, zinc phenolsulphate, hydroxyquinoline, citric acid, lactic acid and pharmaceutically acceptable salts thereof.

The present invention is based on the surprising discovery that combining a nonionic surfactant, which exhibits some anti-stain action itself, with an amino acid, a di- and/or tri-carboxylic acid or a furanolactone substantially reduces the staining on oral surfaces of the bisbiguanide or quaternary ammonium active agents of the instant compositions.

More particularly, the present invention comprises an oral composition useful for controlling dental plaque and gingivitis and for preventing caries which comprises an effective amount of a bisbiguanide or quaternary ammonium compound which is capable of controlling dental plaque and gingivitis and preventing caries and an anti-stain composition which comprises a nonionic surfactant capable of reducing the staining tendency of said bisbiguanide or quaternary ammonium compound and a member selected from the group consisting of an amino acid, a dicarboxylic acid, a tri-carboxylic acid or a mixture of di- and tri-carboxylic acids and a furanolactone, each of which individually inhibits the tendency of bisbiguanides and quaternary compounds to stain oral surfaces.

According to one embodiment of the present invention the antimicrobial agent is a bisbiguanide. More particularly, the 1,1'-bridged-bis[5-higher-alkylbiguanides] and 1,1'-bridged-bis[3-higher alkylguanidines] represented in the free base form by the following structural formula and described in detail in U.S. Pat. No. 3,468,898 have been found to be particularly useful according to the present invention:

$$R-N(R')-\left(\begin{array}{c}NH\\\|\\C-NH\end{array}\right)_x-A-\left(\begin{array}{c}NH\\\|\\NH-C\end{array}\right)_x-N(R')-R$$

wherein the bivalent bridge A is a member of the group consisting of:
(a) alkylene of from 2 to 12 carbon atoms having the valence bonds attached to different carbon atoms, (b) $-(CH_2)_m-Y-(CH_2)_n-$ wherein m and n each represent an integer from 2 to 6 and Y is a member of the group consisting of O and S, (c)

$$-CH_2-CH\begin{array}{c}CH_2-CH_2\\ \\CH_2-CH_2\end{array}CH-CH_2-$$

(d)

[structure showing disubstituted benzene ring with Z and Z' substituents]

wherein Z and Z' are each alkylene of from 1 to 3 carbon atoms, (e)

[structure showing two phenyl rings joined by Q]

wherein Q is a member of the group consisting of $-O-$, $-S-$, $-SO-$ and $-SO_2-$, and (f)

[structure showing two phenyl rings joined by $-CH=CH-$];

R is a member of the group consisting of
(a) alkyl of from 6 to 16 carbon atoms, and
(b) alkyl-Y-alkylene, wherein Y is a member of the group consisting of O and S;
R' is a member of the group consisting of H and lower alkyl; and
x is an integer from 1 to 2.

According to another embodiment of the present invention the antimicrobial agent is a quaternary ammonium compound.

According to another embodiment of the present invention the amount of antimicrobial agent is from 0.01% to about 1.0% w/w based on the total weight of ingredients or w/v when in liquid form.

According to another embodiment of the present invention the amount of anti-stain composition is from 0.1% to 3.5% w/w or w/v.

According to another embodiment of the present invention the pH of the composition is from about 4.8 to about 8.0.

According to another embodiment of the present invention the bisbiguanide is 1,6-bis (2-ethylhexyl-diguanido hexane) dihydrochloride [alexidine dihydrochloride]; 1,6-bis (2-ethylhexyl diguanido hexane) dihydrofluoride; 1,6-bis (2-ethylhexyl diguanido octane) dihydrochloride; 1,6-bis (2-ethylhexyl diguanido nonane) dihydrochloride; 1,6-bis (2-ethylhexyl diguanido dodecane) dihydrochloride; or 1,6-di (4-chlorophenyl diguanido hexane) dihydrochloride or the diacetate or digluconate salt thereof. Alexidine dihydrochloride is especially preferred.

According to another embodiment of the present invention the quaternary ammonium compound is dodecyl dimethyl-(2-phenoxyethyl)-ammonium; benzyldimethyl (2-)2-(p-1,3,3-tetramethyl butyl phenoxy)ethoxyl)ethyl ammonium; p-bromobenzyl-dimethyl-γ-(2'-isopropyl, 4'-chloro, 5'-methylphenoxy)-propyl ammonium; 1-hexadecyl-pyridinium salt; acylcholaminoformylmethyl pyridinium chloride-iodide complex; 1-alkyl-4-aminoquinaldinium salt; decamethyl bis(4-aminoquinaldinium chloride) or hexadecamethylene bis (isoquinolinium chloride).

According to another embodiment of the present invention the nonionic surfactant is a mono- or di-glyceride; a sorbitan fatty acid ester; a polyoxyethylene sorbitan fatty acid ester; a polyoxyethylene sorbitol ester a polyoxyethylene acid; a polyoxyethylene alcohol; a poly(oxyethylene)-poly(oxypropylene)-poly(oxyethylene) polymer; a polyoxyethylene N-substituted fatty acid amide; a poly-(ethylene glycol) p-nonyl phenyl ether; an octyl phenoxy poly ethoxy-ethanol; or a poly siloxane.

According to another embodiment of the present invention the amino acid, which should be compatible with the antimicrobial agent and the nonionic surfactant, is aspartic acid, cysteine, glutamic acid, para-amino benzoic acid, α-aminoadipic acid, N-(p-amino benzoyl) glutamic acid, p-amino hippuric acid or p-amino phenylacetic acid.

According to another embodiment of the present invention the carboxylic acid, which should be compatible with the anti-microbial agent and the nonionic surfactant, is citric acid, α-ketoglutaric acid, malic acid, succinic acid, oxalic acid, adipic acid, fumaric acid, glutaric acid, maleic acid, tartaric acid or malonic acid. Citric acid is preferred According to another embodiment of the present invention the furanolactone, which should be compatible with the antimicrobial agent and the nonionic surfactant, is ascorbic acid.

According to another embodiment of the present invention, the amino acid, the carboxylic acid and the furanolactone are present in a molar excess of about 10:1 to about 25:1 over the cationic antimicrobial agent.

The usual flavoring agents, binders, sudsing agents, humectants, alcohols, fragrances, abrasives and excipients known in the art can be added to the compositions of the present invention.

When the oral composition of the present invention is in the form of a mouthwash, oral rinse or gargle, the composition is brought into contact with the oral cavity and then is expectorated. A dose of 15 to 20 ml. for adults and about 10 ml. for children is generally sufficient when used on a daily basis.

When the instant composition is in the form of a dentifrice, such as a paste, powder, concentrate, solution or gel for direct application to the teeth, it can be used in the normal manner in which a toothpaste is used. When the oral composition of the present invention is in a concentrate for use with mechanical irrigation devices such as a water jet or "water pik" type device, approximately 10 to 15 ml should be sprayed into the mouth and circulated in the oral cavity and then be expectorated. When the present composition is in the form of a breath freshener, either pump spray or aerosol type, approximately 10 to 15 ml. should be sprayed into the mouth, circulated therethrough and be expectorated. When the composition of the present invention is in the form of a troche or a lozenge, it should be allowed to dissolve in the mouth and then be expectorated.

The following nonlimitative examples more particularly illustrate the present invention.

Oral compositions in solution form were produced as follows:

| Examples | 1 | 2 | 3 | 4 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (4) | — | — | — | 0.1–1.5 |
| P-Aminobenzoic Acid | 0.05–1.0 | 0.05–1.0 | 0.05–1.0 | 0.05–1.0 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor / Color | As desired | | | |

| Examples | 5 | 6 | 7 | 8 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (4) | — | — | — | 0.1–1.5 |
| Aspartic Acid | 0.05–1.5 | 0.05–1.5 | 0.05–1.5 | 0.05–1.5 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor | As desired | | | |

-continued

| Examples | 5 | 6 | 7 | 8 |
|---|---|---|---|---|
| Ingredients | % w/v | % w/v | % w/v | % w/v |
| Color | | | | |

| Examples | 9 | 10 | 11 | 12 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (4) | — | — | — | 0.1–1.5 |
| Citric Acid | 0.05–2.0 | 0.05–2.0 | 0.05–2.0 | 0.05–2.0 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor / Color | As desired | | | |

| Examples | 13 | 14 | 15 | 16 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (4) | — | — | — | 0.1–1.5 |
| Fumaric Acid | 0.05–1.0 | 0.05–1.0 | 0.05–1.0 | 0.05–1.0 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor / Color | As desired | | | |

| Examples | 17 | 18 | 19 | 20 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (4) | — | — | — | 0.1–1.5 |
| Gantrez AN-119 (5) | 0.05–0.5 | 0.05–0.5 | 0.05–0.5 | 0.05–0.5 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor / Color | As desired | | | |

| Examples | 21 | 22 | 23 | 24 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (5) | — | — | — | 0.1–1.5 |
| Glutamic Acid | 0.05–1.0 | 0.05–1.0 | 0.05–1.0 | 0.05–1.0 |
| Water to | 100 ml | 100 ml | 100 ml | 100 ml |

| Examples | 21 | 22 | 23 | 24 |
|---|---|---|---|---|
| Ingredients | % w/v | % w/v | % w/v | % w/v |
| NaOH to adjust pH | 4.8–5.1 | 4.8–5.1 | 4.8–5.1 | 4.8–5.1 |
| Flavor | | | | |
| Color | | As desired | | |

| Examples | 25 | 26 | 27 | 28 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (4) | — | — | — | 0.1–1.5 |
| p-hydroxy benzoic acid | 0.05–0.5 | 0.05–0.5 | 0.05–0.5 | 0.05–0.5 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor | | | | |
| Color | | As desired | | |

| Examples | 29 | 30 | 31 | 32 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerine | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (4) | — | — | — | 0.1–1.5 |
| Iminodiacetic Acid | 0.05–0.5 | 0.05–0.5 | 0.05 14 0.5 | 0.05–0.5 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor | | | | |
| Color | | As desired | | |

| Examples | 33 | 34 | 35 | 36 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (4) | — | — | — | 0.1–1.5 |
| Malonic Acid | 0.05–1.0 | 0.05–1.0 | 0.05–1.0 | 0.05–1.0 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor | | | | |
| Color | | As desired | | |

| Examples | 37 | 38 | 39 | 40 |
|---|---|---|---|---|
| Ingredients | % w/v | % w/v | % w/v | % w/v |
| Alexidine . 2HCl | 0.01–0.2 | 0.01–0.2 | 0.01–0.2 | 0.0–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |

-continued

| Examples | 37 | 38 | 39 | 40 |
|---|---|---|---|---|
| Ingredients | % w/v | % w/v | % w/v | % w/v |
| Pluronic F-108 (4) | — | — | — | 0.1–1.5 |
| Mono-tris(hydroxy methyl)amino methane | 0.05–1.0 | 0.05–1.0 | 0.05–1.0 | 0.05–1.0 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor } Color | | As desired | | |

| Examples | 41 | 42 | 43 | 44 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (4) | — | — | — | 0.1–1.5 |
| Pimelic Acid | 0.05–0.5 | 0.05–0.5 | 0.05–0.5 | 0.05–0.5 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor } Color | | As desired | | |

| Examples | 45 | 46 | 47 | 48 |
|---|---|---|---|---|
| Ingredients | % w/v | % w/v | % w/v | % w/v |
| Alexidine . 2HCl | 0.01–0.2 | 0.01–0.2 | 0.01–0.2 | 0.01–0.2 |
| Alcohol USP | 15.0–20.0 | 15.0–20.0 | 15.0–20.0 | 15.0–20.0 |
| Glycerin | 10.0 | 10.0 | 10.0 | 10.0 |
| Sodium Saccharin | 0.002–0.04 | 0.002–0.04 | 0.002–0.04 | 0.002–0.04 |
| Brij-35 S.P. (1) | 0.1–1.5 | — | — | — |
| Tween-80 (2) | — | 0.05–1.0 | — | — |
| Emsorb 6912 (3) | — | — | 0.1–1.5 | — |
| Pluronic F-108 (4) | — | — | — | 0.1–1.5 |
| 2,3-Pyrazinedicarb- oxylic acid | 0.05–0.5 | 0.05–0.5 | 0.05–0.5 | 0.05–0.5 |
| Water to | 100 ml | 100 ml | 100 ml | 100 ml |
| NaOH to adjust pH | 4.8–5.1 | 4.8–5.1 | 4.8–5.1 | 4.8–5.1 |
| Flavor } Color | | As desired | | |

(1) Polyoxyethylene (23) laurylether
(2) Polysorbate-80 USP
(3) Polyoxyethylene (20) Sorbitan Monoisostearate
(4) Poly (oxyethylene) poly (oxypropylene) block copolymer
(5) Copolymer of methyl vinyl ether and maleic anhydride The following in vitro experiments demonstrate the anti-stain effect of the combination of anti-stain agents according to the present invention.

Combinations of Brij 35 S.P. amino or carboxylic acids demonstrated reduction in staining resulting from alexidine dihydrochloride of from 41% to 69%.

Methods

The substrate for the in vitro stain assay was a saliva-coated hydroxylapatite and the staining agent was 5% tannic acid. Each formulation was tested in triplicate. The table set forth below shows the formulation tested and the percent of inhibition of alexidine dihydrochloride mediated stain.

| Formulation | pH | Mole Ratio$^a$ | % Inhibition of Alexidine . 2HCl Mediated Stain |
|---|---|---|---|
| Brij 35 S.P. | 4.8 | — | 30% |
| Citric Acid | 2.4 | | 32% |
| | | 13.8 | |
| Brij 35 S.P. + Citric Acid | 5.1 | | 69% |
| Glutamic Acid | 3.1 | | 40% |
| | | 19.8 | |
| Brij 35 S.P. + Glutamic Acid | 5.1 | | 55% |
| p-Aminobenzoic Acid | 3.5 | | 22% |
| | | 21.2 | |
| Brij 35 S.P. + p-Aminobenzoic acid | 5.1 | | 65% |
| Fumaric Acid | 2.2 | | 44% |
| | | 25.0 | |
| Brij 35 S.P. + Fumaric Acid | 5.0 | | 65% |
| Aspartic Acid | 2.8 | | 34% |

-continued

| Formulation | pH | Mole Ratio[a] | % Inhibition of Alexidine . 2HCl Mediated Stain |
|---|---|---|---|
| | | 21.8 | |
| Brij 35 S.P. + Aspartic Acid | 5.1 | | 41% |

[a]Ratio of amino or carboxylic acid to alexidine . 2HCl.

What is claimed is:

1. An oral composition useful for controlling dental plaque and gingivitis and for preventing caries which comprises from 0.1% to about 1.0% of a cationic antimicrobial agent useful for controlling plaque and gingivitis and for preventing caries selected from the group consisting of a bisbiguanide and a quaternary ammonium compound and from 0.1% to 3.5% of an anti-stain composition which anti-stain composition comprises 0.5% to 1.5% of a nonionic surfactant and 0.5% to 2.0% of ascorbic acid, said ascorbic acid being present in a molar excess of about 10:1 to about 25:1 over the cationic antimicrobial agent, in combination with a pharmaceutically acceptable carrier.

2. A composition according to claim 1 wherein the pH of the composition is from about 4.8 to about 8.0.

3. A composition according to claim 1 wherein the aent is a bisbiguanide which is
1,6-bis (2-ethylhexyl diguanido hexane) dihydrochloride;
1,6-bis (2-ethylhexyl diguanido hexane) dihydrofluoride;
1,6-bis (2-ethylhexyl diguanido octaine) dihydrochloride;
1,6-bis (2-ethylhexyl diguanido nonane) dihydrochloride;
1,6-bis (2-ethylhexyl diguanido dodecane) dihydrochloride; or
1,6-di (4-chlorophenyl diguanido hexane) dihydrochloride or the diacetate or digluconate salt thereof.

4. A composition according to claim 1 wherein the agent is a quaternary ammonium compound which is dodecyl dimethyl-(2-phenoxyethyl)-ammonium; benzyldimethyl (2-)2-(p-1,3,3-tetramethyl butyl phoenxy)ethoxyl)ethyl) ammonium; p-bromobenzyl-dimethyl-γ-(2'-isopropyl, 4'-chloro, 5'-methyl phenoxy)-propyl ammonium; 1-hexadecyl-pyridinium salt; acylcholaminoformyl-methyl pyridinium chloride-iodide complex; 1-alkyl-4-aminoquinaldinium salt; decamethylene bis (4-aminoquinaldinum chloride) or hexadecamethylene bis (isoquinolinium chloride).

5. A composition according to claim 1 wherein the nonionic surfactant is a mono- or di-glyceride; a sorbitan fatty acid ester; a polyoxyethylene sorbitan fatty acid ester; a polyoxyethylene sorbitol ester; a polyoxyethylene acid; a polyoxyethylene alcohol; a poly (oxyethylene)-poly(oxypropylene)-poly(oxyethylene) polymer; a polyoxyethylene N-substituted fatty acid amide; a poly(ethylene glycol) p-nonyl phenyl ether; an octyl phenoxy poly ethoxy-ethanol; or a poly siloxane.

6. A composition according to claim 1 in mouthwash form.

7. A composition according to claim 1 in oral rinse form.

8. A composition according to claim 1 in dentifrice form.

9. A composition according to claim 1 in tooth powder form.

10. A composition according to claim 1 in oral solution form.

11. A composition according to claim 1 in gel form.

12. A composition according to claim 1 in a form suitable for dispensing through a water jet.

13. A composition according to claim 1 in a breath freshener form.

14. A composition according to claim 1 in an aerosol form.

15. A composition according to claim 1 in a gargle form.

16. A composition according to claim 1 in the form of a troche.

17. A composition according to claim 1 in lozenge form.

* * * * *